United States Patent
Laurent et al.

[11] Patent Number: 6,025,376
[45] Date of Patent: *Feb. 15, 2000

[54] CHIRAL METHYLPHENYLOXAZOLIDINONES

[75] Inventors: Henry Laurent; Eckhard Ottow; Gerald Kirsch; Helmut Wachtel; Herbert Schneider, all of Berlin, Germany; Daryl Faulds, Mill Valley; Harald Dinter, San Rafael, both of Calif.

[73] Assignee: Schering Aktiengesellschaft, Berlin, Germany

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/691,651

[22] Filed: Aug. 2, 1996

Related U.S. Application Data

[63] Continuation of application No. 08/599,231, Feb. 9, 1996.

[30] Foreign Application Priority Data

Oct. 20, 1995 [DE] Germany .............................. 195 40 475

[51] Int. Cl.[7] .......................... A61K 31/42; C07D 263/06
[52] U.S. Cl. ............................................ 514/376; 548/232
[58] Field of Search .............................. 548/232; 514/376

[56] References Cited

U.S. PATENT DOCUMENTS

| | | | |
|---|---|---|---|
| 4,012,495 | 3/1977 | Schmiechen et al. | 424/274 |
| 4,153,713 | 5/1979 | Huth et al. . | |
| 4,186,129 | 1/1980 | Huth et al. | 548/186 |
| 4,208,406 | 6/1980 | Lapinet et al. | 424/180 |
| 4,824,838 | 4/1989 | Wachtel et al. | 514/380 |
| 5,227,369 | 7/1993 | Rosen et al. . | |
| 5,420,154 | 5/1995 | Christensen, IV et al. . | |
| 5,541,219 | 7/1996 | Fenton et al. . | |
| 5,672,622 | 9/1997 | Hedgepeth et al. . | |
| 5,783,591 | 7/1998 | Klose et al. . | |

FOREIGN PATENT DOCUMENTS

| | | |
|---|---|---|
| 0411754A2 | 2/1991 | European Pat. Off. . |
| 92/02220 | 2/1992 | WIPO . |
| 92/19594 | 11/1992 | WIPO . |
| 93/167096 | 9/1993 | WIPO . |
| 93/19068 | 9/1993 | WIPO . |

OTHER PUBLICATIONS

Perchellet et al., Cancer Letters, 29:127–137 (1985).
Perchellet et al., Carcinogenesis, 3(10):1149–1158 (1982).
Tonelli et al., Endocrinology, 77:625–634 (Oct. 1965).
Seely et al., Proceedings of the Society for Experimental Biology and Medicine, 159:223–225 (1978).
Jaiswal et al., Journal of Heterocyclic Chemistry, 15(3):519–521 (May 1978).
Multiple Sclerosis and Allied Demyelinative Diseases (1993) *Principles of Neurology*, pp. 777–791 by Adams et al.
Sharief et al. (1991) *New Engl. J. of Medicine*, 325 (7), pp. 467–472.
Benvenuto et al. (1990) *J. Neurol.*, 237 (SUP 1), p. 83 #45.
Kirby et al. (1980) The Lancet, No. 8192 (2), pp. 453–454.
Renz et al. (1988) *J. of Immunology*, pp. 2388–2393.
Marivet et al. (1989) *J. Med. Chem.* 32, pp. 1450–1457.

*Primary Examiner*—Joseph K. McKane
*Assistant Examiner*—Taofiq A. Solola
*Attorney, Agent, or Firm*—Millen, White, Zelano, Branigan, P.C.

[57] ABSTRACT

This invention relates to (R)-(-)-methylphenyloxazolidinone derivatives, a process for their production and their use as pharmaceutical agents.

6 Claims, No Drawings

CHIRAL METHYLPHENYLOXAZOLIDINONES

This application is a continuation application of U.S. Ser. No. 08/599,231, filed on Feb. 9, 1996.

This invention relates to (R)-(−)-methylphenyloxazolidinone derivatives, a process for their production and their use as pharmaceutical agents.

It is known from U.S. Pat. No. 4,186,129 that phenyloxazolidinone derivatives have phosphodiesterase-inhibiting properties and, moreover, have a central-depressive, antidopaminergic, antinociceptive and anticonvulsive effect. EP-0198919 further describes that phenyloxazolidinones in the case of topical application have antiinflammatory properties and EP-0270482 discloses the good neuropsychotropic action of phenyloxazolidinones.

These publications only mention that the separation of the racemate into the antipodes can be carried out with the methods commonly used, without the enantiomers having been indicated and their pharmacological activity studied or the purity of the obtained compounds noted. To reduce the side effects of the pharmaceutical agents, it is desirable to administer a uniformly active substance, which can be used in small dosages.

SUMMARY OF THE INVENTION

It has now been found that R-configured methylphenyloxazolidinone derivatives are especially effective and are better suited for use as pharmaceutical agents than the racemate.

The invention relates to (R)-(−)-methylphenyloxazolidinones of formula I

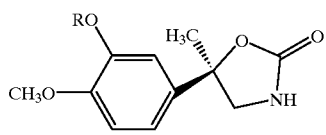

(I)

in which

R means a hydrocarbon radical with up to 5 C atoms.

As a hydrocarbon radical, for example, ethyl, propyl, butyi, isobutyl, isobutenyl, cyclobutyl and cyclopentyl can be mentioned, i.e., alkyl, alkenyl, cycloalkyl, etc.

The compounds of formula I inhibit TNF production and are therefore suitable for treating diseases that are mediated by the activation of TNF. Diseases that are mediated by TNF are defined both as diseases that are triggered by the production of ThF and diseases in which other cytokines, such as, for example, Il-1 or Il-6, are altered by TNF. TNF is defined both as TNF-α and TNF-β, which are both antagonized by the compounds of formula I. Preferably, TNF-α is inhibited.

The compounds of formula I are therefore suitable for the production of a pharmaceutical preparation that is used for the treatment and/or prophylaxis of diseases in living creatures, e.g., humans, which are triggered by stimulation of TNF. Diseases that are altered by excessive or unregulated TNF stimulation include, for example, allergic and inflammatory diseases, auto-immune diseases, pulmonary diseases, infectious diseases and bone resorption diseases, such as rheumatoid arthritis, rheumatoid spondylitis, osteoarthritis, gout, sepsis, septic shock, endotoxin shock, gram-negative sepsis, toxic shock syndrome, ARDS (acute respiratory distress syndrome), pulmonary sarcoidosis, asthma, silicosis, cachexia, ulcerative colitis, Crohn's disease, osteoporosis, organic lesions after reperfusion, inflammatory diseases of the central nervous system such as cerebral malaria, multiple sclerosis, panencephalitis, infectious diseases such as AIDS, bovine insanity, inflammatory diseases of the skin such as urticaria, psoriasis, atopic dermatitis, contact dermatitis, lupus erythematosus as well as diabetes insipidus, neuroprotection, e.g., in the case of Parkinson's disease, dementia, for example, after multiple infarctions and stroke.

The effectiveness of the compounds of formula I in the above-mentioned indications can be shown by appropriate, commonly used pharmacological tests.

The new (R)-(−)-methylphenyloxazolidinones can be obtained from the racemate by chromatography on chiral columins or with diastereomers with optically active adjuvants. As an optically active adjuvant, for example, (R)-1-(1-naphthyl)-ethyl isocyanate is suitable, which makes possible the production of the optically active compound in a simple way in good yields and high purity. The reaction is performed in inert solvents, such as toluene, benzene, i.a., or their mixtures in the presence of an organic base, for example, a tertiary amine such as triethylamine at elevated temperature or boiling temperature of the reaction mixture. The obtained mixture of the diastereomeric allophanates is quantitatively separated into the components by chromatography on silica gel. The separated diastereomeric allophanates are then split into the optically active methylphenyloxazolidinones by treatment with bases, for example, with alkali alcoholates in polar solvents. As polar solvents, for example, cyclic and acyclic ethers, such as tetrahydrofuran, dioxane, diethyl ether, are suitable.

Suitably, the reaction is carried out under inert gas.

The invention also comprises the process for the production of the compounds of formula I, in that their racemate is transferred with an optically active adjuvant into the diastereomeric mixture and then the optically active adjuvant is separated or their racemate is chromatographed on chiral columns. The production of the compounds of formula I can also be carried out by separation of R,S-5-(3-benzyloxy-4-methoxyphenyl)-5-methyl-2-oxazolidinone, for example, by chromatography and subsequent cleavage of the benzyl group and etherification. The cleavage of the benzyl group is carried out, for example, by hydrogenation in the presence of a catalyst, such as, for example, palladium on a suitable vehicle in inert solvents such as ethyl acetate. The subsequent etherification of the hydroxy derivative can be carried out in the presence of bases with a reactive derivative such as a halide, tosylate or mesylate in polar solvents such as dimethylformamide or alcohols at temperatures of up to the boiling point of the solvent. As bases, e.g., alkali compounds such as sodium or potassium hydroxides, -carbonates, -alcoholates or -hydrides are suitable.

If substituent R contains a double bond, the latter can be reduced in the usual way to the corresponding alkyl derivative. For example, the reduction can be carried out catalytically with palladium/carbon in an inert solvent at room temperature or elevated temperature.

The processes according to the invention make possible the production of the compounds of formula I in 99% purity.

In the example of 5-(3-cyclopentyloxy-4-methoxyphenyl)-5-methyl-2-oxazolidinone (compound 1), it can be shown that the (R)-(−)-optically active compound, surprisingly enough, represents the active compound.

The improved effectiveness of the new chiral methylphenyloxazolidinone derivatives in comparison with the racemate can be shown based on the head twitch and grooming reactions in rats that are characteristic of phosphodiesterase type IV (PDE IV) inhibitors. The racemate and the appropriate enantiomers were administered intraperitoneally (i.p.) to male Wistar rats and the occurrence of head twitches and grooming for 15–75 minutes after injection was detected by observation. As can be seen from Table 1, the (+)-enantiomer proved to be 4-fold (head twitches) less effective or 60-fold (grooming) less effective than the racemate, while the (−)-enantiomer was 4-fold stronger (head twitches) or equally active (grooming) in comparison with the racemate.

TABLE 1

| Compound | Head-Twitch Test MED i.p. [mg/kg] | Grooming MED i.p. [mg/kg] |
|---|---|---|
| (R) − (−) − 1 | 0.39 | 0.1 |
| (R,S) − 1 | 1.56 | 0.1 |
| (S) − (+) − 1 | 6.25 | 6.25 |

MED: Minimum effective dose, i.e., the lowest dose that ensures a statistically significant effect.

The action of the enantiomers on the central nervous system was studied in vitro by examining their capacity to displace radiolabeled Rolipram in brain homogenates (Europ. Journ. of Pharmac. Vol. 127, 105–115 (1986)). The $IC_{50}$ values (the concentration at which 50% inhibition action occurs) were converted to inhibition constant $K_i$, which is calculated according to the following formula:

$$K_i = IC_{50}/[1+(L/K_D)],$$

in which L means the concentration of the radioactive tracer and $K_D$ means the dissociation constant of the $^3$H-Rolipram bond, which is determined separately.

TABLE 2

(R)-(−)-Isomer (S)-(−)-Isomer

| R | Racemate $K_i$ (nM) | (R)-(−)-Isomer $K_i$ (nM) | (S)-(+)-Isomer $K_i$ (nM) |
|---|---|---|---|
| Ethyl- | 0.68 | 0.33 | 20 |
| Propyl- | 0.61 | 0.24 | 16 |
| Cyclopentyl- | 0.57 | 0.34 | 3.0 |

Macrophages and microglia cells, which perform macrohage functions in the brain, mediate the release of TNF-α during experimental allergic encephalomyelitis (EAE). If macrophages are stimulated, for example, by lipopolysaccharide (LPS), a secretion of TNF-α is carried out in vitro and in vivo within hours.

A murine macrophage cell line (RAW 264) was preincubated for 30 minutes in the presence and in the absence of various concentrations of PDE-IV inhibitors and then stimulated with LPS (10 ng/ml). 18 hours after stimulation, the culture medium was removed, and the TNF-α release was measured with a specific Elisa test. The test can be obtained from various companies, i.a., from the British biotechnology company Genzyme, and it is carried out as the manufacturer describes.

Table 3 shows the improved TNF-inhibition of the new chiral methylphenyloxazolidinone derivatives in comparison with the racemate in the example of 5-(3-propoxy-4-methoxyphenyl)-5-methyl-2-oxazolidinone (compound 2):

TABLE 3

| Compound | $IC_{50}$ [μM] |
|---|---|
| (RS) − 2 | 0.50 |
| (R) − (−) − 2 | 0.25 |
| (S) − (+) − 2 | 2.50 |

The table shows that the (−)-enantiomer is double as effective as the racemate and 10-fold more effective than the (+)-enantiomer.

Since the new compounds of formula I are distinguished not only by increased effectiveness but also by few side effects and reduced toxicity, the use of (R)-(−)-optically active methylphenyloxazolidinones for the production of pharmaceutical agents is especially advantageous.

The agents are produced according to the usual processes, by the active ingredient being put into the form of a pharmaceutical preparation that is suitable for enteral or parenteral administration, with suitable vehicles, adjuvants and/or additives. The preparations thus obtained can be used as pharmaceutical agents in human or veterinary medicine. Administration can be done orally or sublingually as a solid in the form of capsules or tablets or as a liquid in the form of solutions, suspensions, elixirs, aerosols or emulsions, or rectally in the form of suppositories, or in the form of injection solutions that can optionally also be administered subcutaneously, intramuscularly or intravenously, or topically or intrathecally. As adjuvants for the desired pharmaceutical agent formulation, inert organic and inorganic media that are known to one skilled in the art, such as, e.g., water, gelatin, gum arabic, lactose, starch, magnesium stearate, talc, vegetable oils, polyalkyleneglycols, etc., are suitable. Moreover, preservatives, stabilizers, wetting agents, emulsifiers or salts can optionally be contained to alter the osmotic pressure or buffer.

The pharmaceutical preparations can be present in solid form, for example, as tablets, coated tablets, suppositories, capsules or in liquid form, e.g., as solutions, suspensions or emulsions.

As vehicle systems, near-interface adjuvants such as salts, bile acids or animal or plant phospholipids and mixtures of them as well as liposomes or their components can also be used.

For oral administration, especially tablets, coated tablets or capsules with talc and/or hydrocarbon vehicles or binders, such as, e.g., lactose, corn or potato starch, are especially suitable. Application can also be done in liquid form, such as, e.g., in the form of juice, to which sweetener is optionally added.

The compounds of formula I are used in dosages that are sufficient to reduce the TNF production to normal levels or below.

The dosage of the active ingredients can vary depending on the method of administration, the age and weight of the patient, the type and severity of the disease to be treated and similar factors. The daily dose for an adult human is 0.1–25 mg, preferably 0.5–5 mg, whereby the dose can be given as a single dose to be administered one time or divided into 2 or more daily doses. The compounds can be used analogously to those described in U.S. Ser. No. 327,478 of Oct. 21, 1994, and U.S. Ser. No. 284,527 of Jul. 28, 1994.

The entire disclosure of U.S. Ser. No. [Attorney Docket No. SCH 1522] filed on even date, it incorporated by reference herein.

In so far as the production of the starting compounds is not described, the latter are known from the mentioned publications or can be produced analogously to the known compounds or processes that are described here.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application 195 40 475.0, filed Oct. 20, 1995, are hereby incorporated by reference.

The following examples are to explain the process according to the invention.

STARTING COMPOUNDS

(R,S)-2-(3-Cyclopentyloxy-4-methoxyphenyl)-2-hydroxy-1-propylamine 16.9 g of 3-cyclopentyloxy-4-methoxy-acetophenone is dissolved with heating in 12.5 ml of trimethylsilyl cyanide. After the addition of 700 mg of zinc iodide, a strong heat shading occurs; then it is cooled to 20° C. and stirred for 30 minutes under nitrogen. The reaction mixture is mixed with 100 ml of tetrahydrofuran and instilled within 20 minutes in a solution of 4.4 g of lithium alanate in 100 ml of tetrahydrofuran. After another 30 minutes, 100 ml of a saturated potassium sodium tartrate solution is carefully added. A pulpy material is formed, from which the tetrahydrofuran phase can be decanted. The pulpy residue is extracted seven times with 100 ml of diethyl ether each, the extracts are concentrated by evaporation in a vacuum together with the tetrahydrofuran phase. The residue is dissolved in 300 ml of ethyl acetate and extracted three times with 50 ml of 2N hydrochloric acid each. The combined acid extracts are set at pH 13 with 4N sodium hydroxide solution and extracted six times with 100 ml of diethyl ether each. The ether extracts are dried on sodium sulfate and concentrated by evaporation in a vacuum. 16.4 g of (R,S)-2-(3-cyclopentyloxy-4-methoxyphenyl)-2-hydroxy-1-propylamine with a melting point of 82° C. is obtained as residue.

(R,S)-5-(3-Cyclopentyloxy-4-methoxyphenyl)-5-methyl-2-oxazolidinone

A solution of 16.4 g of (R,S)-2-(3-cyclopentyloxy-4-methoxyphenyl)-2-hydroxy-1-propylamine in 150 ml of tetrahydrofuran is mixed with 10.2 g of N,N'-carbonyldiimidazole and stirred for 3 hours at room temperature. The reaction mixture is concentrated by evaporation in a vacuum, the residue is dissolved in 500 ml of ethyl acetate, and the solution is washed twice with 50 ml of 2N hydrochloric acid each and then with water, dried and concentrated by evaporation in a vacuum. 17.7 g of (R,S)-5-(3-cyclopentyloxy-4-methoxyphenyl)-5-methyl-2-oxazolidinone is obtained as residue. Melting point 83.5° C.

(R,S)-2-(4-Methoxy-3-propoxyphenyl)-2-hydroxy-1-propylamine

A mixture of 30 g of 4-methoxy-3-propoxy-acetophenone and 25 ml of trimethylsilyl cyanide is mixed with 1.4 g of zinc iodide and heated for 4 hours to 110° C. After cooling, the reaction mixture is diluted with 200 ml of tetrahydrofuran, mixed drop by drop with a suspension of 8.0 g of lithium alanate in 200 ml of tetrahydrofuran and heated to boiling for one hour. After cooling to 4° C., it is diluted with 750 ml of diethyl ether, and the mixture is then carefully mixed with saturated sodium bicarbonate solution over a period of 45 minutes until solid aluminum hydroxide separates. The organic phase is separated, and the remaining inorganic material is washed with 1000 ml of diethyl ether. The combined organic phases are concentrated by evaporation in a vacuum, the residue is taken up in dichloromethane and extracted four times with 80 ml of aqueous 2N hydrochloric acid each. The combined acid aqueous phases are brought to pH 10 with aqueous 5N sodium hydroxide solution, and, after saturation with sodium chloride, repeatedly extracted with ethyl acetate. The combined extracts are dried on sodium sulfate and concentrated by evaporation in a vacuum. 25.0 g of (R,S)-2-(4-methoxy-3-propoxyphenyl)-2-hydroxy-1-propylamine with a melting point of 90° C. is obtained as residue.

(R,S)-5-(4-Methoxy-3-propoxyphenyl)-5-methyl-2-oxazolidinone

While being cooled with ice, a solution of 24.0 g of (R,S)-2-(4-Methoxy-3-propoxyphenyl)-2-hydroxy-1-propylamine in 260 ml of tetrahydrofuran is mixed with 19.4 g of N,N'-carbonyldiimidazole and then stirred for 16 hours at room temperature. The solvent is evaporated in a vacuum, the residue is dissolved in 300 ml of ethyl acetate and the solution is washed three times with 50 ml of aqueous 1N hydrochloric acid each. Then, the organic phase is washed with sodium bicarbonate solution as well as with sodium chloride solution, dried on sodium sulfate and concentrated by evaporation in a vacuum. The oily residue of 28 g is purified by chromatography on a silica gel column, with a hexane-ethyl acetate mixture as eluant. 24.5 g of (R,S)-5-(4-methoxy-3-propoxyphenyl)-5-methyl-2-oxazolidinone results. Melting point 71° C.

(R,S)-2-(3-Ethoxy-4-methoxyphenyl)-2-hydroxy-1-propylamine

A mixture of 28 g of 3-ethoxy-4-methoxy-acetophenone and 25 ml of trimethylsilyl cyanide is mixed with 1.4 g of zinc iodide and heated for 4 hours to 100° C. After cooling, the reaction mixture is diluted with 200 ml of tetrahydrofuran, mixed drop by drop with a suspension of 8.0 g of lithium alanate in 200 ml of tetrahydrofuran and heated to boiling for one hour. After cooling to 4° C., it is diluted with 750 ml of diethyl ether, and the mixture is then carefully mixed with saturated sodium bicarbonate solution over a period of 45 minutes until aluminum hydroxide separates. The organic phase is separated and the remaining inorganic material is washed with 1000 ml of diethyl ether. The combined organic phases are concentrated by evaporation in a vacuum, the residue is taken up in dichloromethane and extracted four times with 80 ml of aqueous 2N hydrochloric acid each. The combined acid aqueous phases are brought to pH 10 with aqueous 5N sodium hydroxide solution and, after saturation with sodium chloride, extracted repeatedly with ethyl acetate. The combined extracts are dried on sodium sulfate and concentrated by evaporation in a vacuum. 26.1 g of (R,S)-2-(3-ethoxy-4-methoxyphenyl)-2-hydroxy-1-propylamine with a melting point of 88° C. is obtained as residue.

(R,S)-5-(3-Ethoxy-4-methoxyphenyl)-5-methyl-2-oxazolidinone

While being cooled with ice, a solution of 11.2 g of (R,S)-2-(3-ethoxy-4-methoxyphenyl)-2-hydroxy-l-propylamine in 130 ml of tetrahydrofuran is mixed with 9.7 g of N,N'-carbonyldiimidazole and then stirred for 16 hours at room temperature. The solvent is evaporated in a vacuum, the residue is dissolved in 200 ml of ethyl acetate and the solution is washed twice with 50 ml of aqueous 1N hydrochloric acid each. Then, the organic phase is washed with sodium bicarbonate solution and sodium chloride solution, dried on sodium sulfate and concentrated by evaporation in a vacuum. The oily residue of 12 g is purified by chromatography on a silica gel column, with a hexane-ethyl acetate mixture as eluant. 9.6 g of (R,S)-5-(3-ethoxy-4-methoxyphenyl)-5-methyl-2-oxazolidinone results. Melting point 102° C.

EXAMPLE 1

Preparation and Separation of Diastereomeric Allophanates 17.7 g of (R,S)-5-(3-cyclopentyloxy-4-methoxyphenyl)-5-methyl-2-oxazolidinone is dissolved in 240 ml of toluene. After the addition of 9 ml of triethylamine and 12.8 g of (R)-1-(1-naphthyl)-ethyl isocyanate, the reaction solution is heated to boiling for 17 hours under nitrogen and then concentrated by evaporation in a vacuum. The residue of 31.1 g is chromatographed on a silica gel column (Kromasil, 10 μm) with a hexane-diethyl ether mixture (6:4). 11.5 g of N-[(R)-1-(1-naphthyl)ethyl]-(R)-5-(3-cyclopentyloxy-4-methoxyphenyl)-5-methyl-2-oxazolidinone-3-carboxylic acid amide, melting point 124° C., $[\alpha]_D$=−8° (CHCl$_3$), as well as 13.5 g of N-[(R)-1-(1-naphthyl)ethyl]-(S)-5-(3-cyclopentyloxy-4-methoxyphenyl)-5-methyl-2-oxazolidinone-3-carboxylic acid amide, in oily form, $[\alpha]_D$=−41° (CHCl$_3$), are eluted.

(R)-(−)-5-(3-Cyclopentyloxy-4-methoxyphenyl)-5-methyl-2-oxazolidinone

While being cooled with ice and in a nitrogen atmosphere, a solution of 11.0 g of N-[(R)-1-(1-naphthyl)ethyl]-(R)-5-(3-cyclopentyloxy-4-methoxyphenyl)-5-methyl-2-oxazolidinone-3-carboxylic acid amide in 230 ml of tetrahydrofuran is mixed with 2.3 g of potassium ethylate and stirred for 30 minutes at room temperature. After the addition of 700 ml of ethyl acetate, it is washed twice with 50 ml of 2N hydrochloric acid each and then with water, dried and concentrated by evaporation in a vacuum. The crude product of 12.3 g is chromatographed on a silica gel column (Kromasil, 10 μm) with an ethyl acetate-hexane mixture (3:7). 6.68 g is eluted and recrystallized from hexane-dichloromethane.

Yield: 6.23 g of (R)-(−)-5-(3-cyclopentyloxy-4-methoxyphenyl)-5-methyl-2-oxazolidinone. Melting point 84° C. $[\alpha]_D$=−41° (CHCl$_3$).

(S)-(+)-5-(3-Cyclopentyloxy-4-methoxyphenyl)-5-methyl-2-oxazolidinone

A solution of 490 mg of N-[(R)-1-(1-naphthyl)ethyl]-(S)-5-(3-cyclopentyloxy-4-methoxyphenyl)-5-methyl-2-oxazolidinone-3-carboxylic acid amide in 10 ml of tetrahydrofuran is mixed in a nitrogen atmosphere with 90 mg of potassium ethylate and stirred for one hour at room temperature. After the addition of 50 ml of ethyl acetate, it is washed twice with 10 ml of 2N hydrochloric acid each and then with water, dried and concentrated by evaporation in a vacuum. The crude product of 470 mg is chromatographed on a silica gel column (Kromasil, 10 μm) with an ethyl acetate-hexane mixture (3:7). 260 mg of crystalline (S)-(+)-5-(3-cyclopentyloxy-4-methoxyphenyl)-5-methyl-2-oxazolidinone is eluted. Melting point 80° C. $[\alpha]_D$=+38° (CHCl$_3$).

EXAMPLE 2

Preparation and Separation of Diastereomeric Allophanates 14.6 g of (R,S)-5-(4-methoxy-3-propoxyphenyl)-5-methyl-2-oxazolidinone is dissolved in 200 ml of toluene. After the addition of 7.7 ml of triethylamine and 10.0 g of (R)-1-(1-naphthyl)-ethyl isocyanate, the reaction solution is heated to boiling for 16 hours under nitrogen. After cooling to room temperature, it is concentrated by evaporation in a vacuum, the residue is dissolved in ethyl acetate, solid components are filtered out and the solution is concentrated in a vacuum. The residue is chromatographed on a silica gel column (Kromasil, 10 μm) with an ethyl acetate-hexane mixture (3:7). 10.9 g is eluted. After recrystallization from ethyl acetate-hexane, 7.0 g of N-[(R)-1-(1-naphthyl)ethyll-(R)-5-(4-methoxy-3-propoxyphenyl)-5-methyl-2-oxazolidinone-3-carboxylic acid amide is obtained. Melting point 106° C. $[\alpha]_D$=−9° (CHCl$_3$). Further, 12.4 g of N-[(R)-1-(1-naphthyl)ethyl]-(S)-5-(4-methoxy-3-propoxyphenyl)-5-methyl-2-oxazolidinone-3-carboxylic acid amide is eluted as oil. $[\alpha]_D$=−43° (CHCl$_3$).

(R)-(−)-5-(4-Methoxy-3-propoxyphenyl)-5-methyl-2-oxazolidinone

While being cooled with ice, a solution of 10.0 g of N-[(R)-1-(1-naphthyl)ethyl]-(R)-5-(4-methoxy-3-propoxyphenyl)-5-methyl-2-oxazolidinone-3-carboxylic acid amide in 200 ml of tetrahydrofuran is mixed with 2.3 g of potassium ethylate and then stirred at room temperature for 1.5 hours. After the addition of 400 ml of ethyl acetate, it is washed twice with 50 ml of 2N hydrochloric acid each and then with water, dried and concentrated by evaporation in a vacuum. The crude product of 8.3 g is chromatographed on a silica gel column with a mixture of ethyl acetate and hexane as eluant. 5.3 g of (R)-(−)-5-(4-methoxy-3-propoxyphenyl)-5-methyl-2-oxazolidinone, which is recrystallized from an ethyl acetate-hexane mixture, is obtained. Yield: 4.5 g. Melting point 93° C. $[\alpha]_D$=−48° (CHCl$_3$).

(S)-(+)-5-(4-Methoxy-3-propoxyphenyl)-5-methyl-2-oxazolidinone

While being cooled with ice, a solution of 13.8 g of N-[(R)-1-(1-naphthyl)ethyl]-(S)-5-(4-methoxy-3-propoxyphenyl)-5-methyl-2-oxazolidinone-3-carboxylic acid amide in 200 ml of tetrahydrofuran is mixed with 4.8 g of potassium ethylate and then stirred at room temperature for 16 hours. After the addition of 400 ml of ethyl acetate, it is washed twice with 50 ml of 2N hydrochloric acid each and then with water, dried and concentrated by evaporation in a vacuum. The crude product of 16.5 g is chromatographed on a silica gel column with a mixture of ethyl acetate and hexane as eluant. 8.3 g of (S)-(+)-5-(4-methoxy-3-propoxyphenyl)-5-methyl-2-oxazolidinone is obtained.

After crystallization from hexane-ethyl acetate, 6.4 g remains. Melting point 94° C. $[\alpha]_D$=+45° (CHCl$_3$).

EXAMPLE 3

Preparation and Separation of Diastereomeric Allophanates 5.9 g of (R,S)-5-(3-ethoxy-4-methoxyphenyl)-5-methyl-2-oxazolidinone is dissolved in 90 ml of toluene. After the addition of 3.3 ml of triethylamine and 4.8 g of (R)-1-(1-naphthyl)-ethyl isocyanate, the reaction solution is heated to boiling for 25 hours under nitrogen. After cooling to room temperature, it is concentrated by evaporation in a vacuum, the residue is dissolved in ethyl acetate, solid components are filtered out and the solution is concentrated in a vacuum. The residue is chromatographed on a silica gel column (Kromasil, 10 µm) with an ethyl acetate-hexane mixture (3:7). 4.55 g of N-((R)-1-(1-naphthyl)ethyl]-(R)-5-(3-ethoxy-4-methoxyphenyl)- 5-methyl-2-oxazolidinone-3-carboxylic acid amide is eluted. Melting point 112° C. $[\alpha]_D$=−12° (CHCl$_3$). Further, 4.4 g of N-[(R)-1-(1-naphthyl)ethyl]-(S)-5-(3-ethoxy-4-methoxyphenyl)-5-methyl-2-oxazolidinone-3-carboxylic acid amide is eluted as oil. $[\alpha]_D$=39° (CHCl$_3$).

(R)-(−)-5-(3-Ethoxy-4-methoxyphenyl)-5-methyl-2-oxazolidinone

While being cooled with ice, a solution of 7.3 g of N-[(R)-1-(1-naphthyl) ethyl]-(R)-5-(3-ethoxy-4-methoxyphenyl)-5-methyl-2-oxazolidinone-3-carboxylic acid amide in 100 ml of tetrahydrofuran is mixed with 1.8 g of potassium ethylate and then stirred for 30 minutes at room temperature. After the addition of 300 ml of ethyl acetate, it is washed twice with 50 ml of 2N hydrochloric acid each and then with water, dried and concentrated by evaporation in a vacuum. The crude product is chromatographed on a silica gel column with a mixture of ethyl acetate and hexane as eluant. 3.8 g of (R)-(−)-5-(3-ethoxy-4-methoxyphenyl)-5-methyl-2-oxazolidinone is obtained. After recrystallization from hexane-ethyl acetate, 3.1 g remains. Melting point 87° C. $[\alpha]_D$=−51° (CHCl$_3$).

(S)-(+)-5-(3-Ethoxy-4-methoxyphenyl)-5-methyl-2-oxazolidinone

While being cooled with ice, a solution of 10.1 g of N-[(R)-1-(1-naphthyl)ethyl]-(S)-5-(3-ethoxy-4-methoxyphenyl)-5-methyl-2-oxazolidinone-3-carboxylic acid amide in 200 ml of tetrahydrofuran is mixed with 3.6 g of potassium ethylate and then stirred for 16 hours at room temperature. After the addition of 400 ml of ethyl acetate, it is washed twice with 50 ml of 2N hydrochloric acid each and then with water, dried and concentrated by evaporation in a vacuum. The crude product of 11.5 g is chromatographed on a silica gel column with a mixture of ethyl acetate and hexane as eluant. 5.5 g of (S)-(+)-5-(3-ethoxy-4-methoxyphenyl)-5-methyl-2-oxazolidinone is obtained. After recrystallization from hexane-ethyl acetate, 4.1 g remains. Melting point 85° C. $[\alpha]_D$=+49° (CHCl$_3$).

EXAMPLE 4

Separation of the diastereomers of (R,S)-5-(3-benzyloxy-4-methoxyphenyl)-5-methyl-2-oxazolidinone 3 g of (R,S)-5-(3-benzyloxy-4-methoxyphenyl)-5-methyl-2-oxazolidinone is chromatographed on a Chirapher column (25 µm) in a Procrom unit with a hexane-dioxane mixture. 1.2 g of (S)-(+)-5-(3-benzyloxy-4-methoxyphenyl)-5-methyl-2-oxazolidinone, melting point 116.8° C., $[\alpha]_D$=+38.9° (CHCl$_3$), as well as 1.1 g of (R)-(−)-5-(3-benzyloxy-4-methoxyphenyl)-5-methyl-2-oxazolidinone, melting point 116.7° C., $[\alpha]_D$=+38.4° (CHCl$_3$), are eluted.

(R)-(−)-5-(3-Hydroxy-4-methoxyphenyl)-5-methyl-2-oxazolidinone 1.1 g of (R)-(−)-5-(3-benzyloxy-4-methoxyphenyl)-5-methyl-2-oxazolidinone is dissolved in 40 ml of ethyl acetate and mixed with 100 mg of palladium/10% carbon. It is hydrogenated until hydrogen absorption is completed. After filtration on silica gel and concentration by evaporation in a vacuum, 750 mg of (R)-(−)-5-(3-hydroxy-4-methoxyphenyl)-5-methyl-2-oxazolidinone, melting point 141.6° C., is obtained. $[\alpha]_D$=−28.2° (CHCl$_3$).

(R)-(−)-5-(3-Cyclobutyloxy-4-methoxyphenyl)-5-methyl-2-oxazolidinone

A solution of 80 mg of (R)-(−)-5-(3-hydroxy-4-methoxyphenyl)-5-methyl-2-oxazolidinone is mixed in 1 ml of dimethylformamide with 25 mg of 55–65% sodium hydride and stirred for 15 minutes at 60° C. After cooling, 0.04 ml of bromocyclobutane is instilled and stirred for 2 hours at 110° C. The reaction mixture is evaporated to dryness in an oil vacuum on a bulb tube. The residue is purified by chromatography on a silica gel column, with a hexane-ethyl acetate mixture as eluant.

52 mg of (R)-(−)-5-(3-cyclobutyloxy-4-methoxyphenyl)-5-methyl-2-oxazolidinone, melting point 132.5° C., results. $[\alpha]_D$=−38.6° (CHCl$_3$).

EXAMPLE 5

(R)-(−)-5-(3-Isobutenyloxy-4-methoxyphenyl)-5-methyl-2-oxazolidinone

A solution of 710 mg of (R)-(−)-5-(3-hydroxy-4-methoxyphenyl)-5-methyl-2-oxazolidinone in 30 ml of ethanol is mixed in succession with 658 mg of potassium carbonate and 0.48 ml of methallyl chloride. After 15 hours of stirring, it is filtered at 70° C. and the solution is concentrated by evaporation in a vacuum. The oily residue is purified by chromatography on a silica gel column with a hexane-ethyl acetate mixture as eluant. 620 mg of (R)-(−)-5-(3-isobutenyloxy-4-methoxyphenyl)-s-methyl-2-oxazolidinone, in oily form, results. $[\alpha]_D$=−24.3°.

EXAMPLE 6

(R)-(−)-5-(3-Isobutyloxy-4-methoxyphenyl)-5-methyl-2-oxa-zolidinone 360 mg of (R)-(−)-5-(3-isobutenyloxy-4-methoxyphenyl)-5-methyl-2-oxazolidinone is dissolved in 10 ml of ethyl acetate and mixed with 50 mg of palladium/10% carbon. It is hydrogenated until hydrogen absorption is completed. After filtration on diatomaceous earth and concentration by evaporation in a vacuum, an oily residue is obtained. The crude product is purified by chromatography on a silica gel column, with a hexane-acetone mixture as eluant. 186 mg of (R)-(−)-5-(3-isobutyloxy-4-methoxyphenyl)-5-methyl-2-oxazolidinone, melting point 93.7° C., results. $[\alpha]_D$=−24.7°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for treating a disease that is mediated by the activation of the tumor necrosis factor, comprising administering to a patient in need of such treatment an amount effective to inhibit TNF or its production of (R)-(−)-methylphenyloxazolidinone of formula I

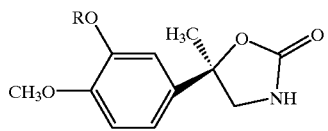

in which

R is a hydrocarbon of up to 5 C atoms, with the proviso that said compound is not administered locally to treat inflammation.

2. A method for treating a disease that is mediated by the activation of the tumor necrosis factor comprising administering to a patient in need of such treatment an amount effective to inhibit TNF or its production of
- (R)-(−)-5-(3-Cyclopentyloxy-4-methoxyphenyl)-5-methyl-2-oxazolidinone,
- (R)-(−)-5-(3-ethoxy-4-methoxyphenyl)-5-methyl-2-oxazolidinone, or
- (R)-(−)-5-(3-propoxy-4-methoxyphenyl)-5-methyl-2-oxazolidinone.

3. A method for treating multiple sclerosis comprising administering to a patient in need of such treatment an effective amount of (R)-(−)-methylphenyloxazolidinone of formula I

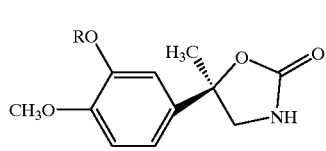

in which

R is a hydrocarbon of up to 5 C atoms, with the proviso that said compound is not administered locally to treat inflammation.

4. A method for treating multiple sclerosis comprising administering to a patient in need of such treatment an effective amount of
- (R)-(−)-5-(3-Cyclopentyloxy-4-metboxyphenyl)-5-methyl-2-oxazolidinone,
- (R)-(−)-5-(3-ethoxy-4-methoxyphenyl)-5-methyl-2-oxazolidinone, or
- (R)-(−)-5-(3-propoxy-4-methoxyphenyl)-5-methyl-2-oxazolidinone.

5. The method of claim 2, wherein the compound administered is (R)-(−)-5-(3-propoxy-4-methoxyphenyl)-5-methyl-2-oxazolidinone.

6. The method of claim 4, wherein the compound administered is (R)-(−)-5-(3-propoxy-4-methoxyphenyl)-5-methyl-2-oxazolidinone.

* * * * *